(12) United States Patent
Ceres et al.

(10) Patent No.: US 6,500,464 B2
(45) Date of Patent: Dec. 31, 2002

(54) BILAYERED COLLAGEN CONSTRUCT

(75) Inventors: Ralph A. Ceres, Nutley, NJ (US);
David J. Brown, New York, NY (US);
Daniel C. Lesnoy, Fair Lawn, NJ (US)

(73) Assignee: Ortec International, Inc., New York, NY (US)

( * ) Notice: Subject to any disclaimer, the term of this patent is extended or adjusted under 35 U.S.C. 154(b) by 0 days.

(21) Appl. No.: 09/751,001

(22) Filed: Dec. 28, 2000

(65) Prior Publication Data

US 2002/0085994 A1 Jul. 4, 2002

(51) Int. Cl.⁷ .............................................. A61K 38/39
(52) U.S. Cl. ..................... 424/543; 424/548; 424/422; 424/423; 424/426; 424/443; 424/444; 424/93.7; 514/2; 514/21; 514/953; 623/11; 623/15
(58) Field of Search ................................. 424/543, 548, 424/422, 423, 426, 443, 444, 93.7; 514/2, 21, 953; 623/11, 15

(56) References Cited

U.S. PATENT DOCUMENTS 5,282,859 A * 2/1994 Eisenberg .................... 623/11

* cited by examiner

Primary Examiner—Jean C. Witz
(74) Attorney, Agent, or Firm—Ralph T. Lilore

(57) ABSTRACT

This invention describes a collagen construct uniquely suited as a substrate for production of biologically active wound dressings, skin equivalents or skin substitutes. The collagen construct of the invention comprises a porous collagen sponge and a cell-impermeable transitional layer between the sponge and the boundary surface of the cell-impermeable transitional layer. Optionally, a further layer conducive to the attachment of cells, e.g. keratinocytes, may be coated as a third layer on the cell-impermeable layer. The sponge layer may be seeded with dermal cells, or other suitable cells and the boundary surface or the third layer may be seeded with epithelial cells, e.g. keratinocytes. The process used for the production of this construct also is described.

20 Claims, 3 Drawing Sheets

BILAYERED COLLAGEN CONSTRUCT

FIELD OF THE INVENTION

This invention relates to biologically active wound dressings and more particularly to biologically active bilayered constructs useful as a wound dressing, as a skin equivalents or as skin substitutes. It relates also to the manufacture of such constructs in an economical, large scale, process.

BACKGROUND

Burn wounds, in general, are exceedingly painful and difficult to heal. Burns can be partial thickness burns, which destroy some, but not all of the epidermis and may destroy a portion of the dermis. Some partial thickness burn wounds will heal if treated properly with bioactive dressings, which can protect the wound and promote rapid epithelialization with minimal inflammation and scar formation. Full thickness burns, on the other hand, destroy all of the epidermis, the hair follicles, sweat glands and sebaceous glands and frequently much of the dermis. Full thickness burns ultimately require skin grafting.

Several types of skin grafts have been used to cover and repair damaged skin. Autografts are the most effective skin grafts and are tissue transplants derived from the injured individual, usually in the form of split-thickness skin grafts. A split-thickness skin graft consists of skin removed from a donor site and placed on a full thickness wound, after debridement of the dead tissue, to close and heal the wound. Split-thickness skin grafts, comprise the epidermis, part of the epidermal adnexal structures and part of the dermis. Typically, a split-thickness skin graft is meshed (short, alternating incisions) which allows for a maximum of 1:10 expansion of the graft tissue and usually an expansion of 1:3 or less. Other types of skin grafts include allografts, which are tissue transplants between individuals of the same species but different genotypes, and homografts, which are allografts from humans. Harvesting these grafts creates additional skin wounds which, in turn, need to be treated and may compromise the patient further.

Disadvantages of skin grafts, other than autografts, include infection and frequent rejection by the recipient requiring the use of immunosuppressive agents. Research efforts have been directed towards developing functional substitutes, that overcome the disadvantages of skin substitutes derived from animal skin, to provide permanent wound closure.

An effective bioactive wound dressing should facilitate the repair of wounds that may require restoration of both the epidermis and dermis. To be successful such a skin graft must be placed onto, and be accepted by, the debrided wound of the recipient and provide a means for the permanent re-establishment of the dermal and epidermal components of skin. The graft should not evoke an immune response, which can destroy the graft, and should include suitable dermal components to support the growth and development of a normal epidermis. The graft should suppress the formation of granulation tissue which causes scarring.

Additional criteria for biologically active wound dressings include: rapid adherence to the wound soon after placement; proper vapor transmission to control evaporative fluid loss from the wound and to avoid the collection of exudate between the wound and the dressing material. Skin substitutes should act as barrier to microorganisms, limit the growth of microorganisms already present in the wound, be flexible, durable and resistant to tearing. The substitute should exhibit tissue compatibility, that is, it should not provoke inflammation or foreign body reaction in the wound which may lead to the formation of granulation tissue. An inner surface structure should be provided that permits ingrowth of fibro-vascular tissue. An outer surface structure should be provided to minimize fluid transmission and promote. epithelialization. A variety of materials and constructions have been proposed to meet these requirements.

Synthetic polymeric materials in various forms have been tested for the development of skin structures having the ability to induce cellular migration and proliferation into the graft. This effort has been limited by the high incidence of infection and inability to promote vascularization and epithelialization. Epithelialization of the membrane graft provides a barrier to infection and contributes to the control of fluid loss.

Typical bioabsorbable materials for use in the fabrication of porous wound dressings, skin substitutes and the like, include synthetic bioabsorbable polymers such as polylactic acid or polyglycolic acid, and also, biopolymers such as the structural proteins and polysaccharides. Skin substitutes made from synthetic polymers have, for a number of reasons, met with limited success. The structural proteins have also met with limited success and include collagen, elastin, fibronectin, laminin and fibrin, as well as other proteins of the human connective tissue matrix. Of these, the material most studied has been collagen. Collagen is the most abundant animal protein and the major protein of skin and connective tissue. A high degree of homology exists between the various types of collagen found in different animal species and human collagen. Accordingly, animal collagen types such as bovine collagen are useful because they exhibit very low immunogenicity when implanted into humans or used as topical dressings on human wounds.

However, the use of collagen alone as a reconstituted collagen film, sponge or sheet for example, has not been demonstrated to serve as an effective wound covering for various reasons among which are the stimulation of the development of granulation tissue and production of a chronic inflammatory response before being resorbed or biodegraded.

Besides films or sheets, collagen may be prepared in a variety of physical forms including porous mats and sponges. Freeze drying an aqueous gel or an aqueous suspension of collagen may be used to produce a porous collagen sponge. Such collagen sponges are described, for example, by Chvapil and co-workers in J. Biomed. Mater. Res. 11 721–741 (1977).

Porous implants, made from biological, bioabsorbable components, are normally intended to be invaded by the cells of the host or recipient of the implant. By and large, these sponges have not proven to be very useful. Later developments, using sponges of appropriate structure and inoculated with suitable cell types have, however, shown considerable promise.

The prior art processes for preparation of a cell-impermeable film on a surface of lyophilized collagen sponge to support and anchor a cellular component, e.g. keratinocytes, generally done using complex and technically difficult procedures. Earlier work by others in this field includes the following:

Yannas, (U.S. Pat. No. 4,060,081) teaches the preparation of a fibrous layer of a mixture of collagen and chondroitin-6-sulfate (GAG) to which is attached a silicone component. The collagen/GAG component of this skin substitute was found to be biodegradable and was said not to be inflammatory or immunogenic. However, it required that the silicone "epidermis" be removed at a later date and that the dermal layer be covered with a thin autograft, to provide the epidermal component, for permanent wound closure.

In U.S. Pat. No. 4,505,266, Yannas discloses the preparation of a cross-linked, bi-layer sponge which has a silicone membrane coated on its surface to serve as a moisture barrier. A milled collagen dispersion is blended with chrondroitin 6-sulfate and the mixture poured into freezing trays. This was then lyophilized for a period of 24 to 48 hours to form a porous structure. When the lyophilization was complete, the sponge was cross-linked by heating for about 24 hours at 105° C. Finally a silicone adhesive was coated over the entire exposed surface of the cooled foam. After curing, the silicone formed an impermeable layer.

Berg discloses a surface coating of a collagen construct with a noncollagenous, non-bioabsorbable adhesive (U.S. Pat. No. 4,841,962).

Ksander, in U.S. Pat. No. 4,950,483, discloses that multilayer atelopeptide collagen sponge products can be formed by serially casting and flash freezing each layer as it is applied. This was followed by lyophilizing and drying the plurality of layers. This process lyophilizes the combined layers and makes them porous. There does not appear to be an impermeable layer.

Silver describes a biodegradable collagen construct allegedly suitable for use as a wound implant (U.S. Pat. No. 4,970,298). The construct was formed by freeze drying an aqueous dispersion containing collagen, cross-linking the collagen via two cross-linking steps and freeze-drying the cross-linked matrix.

The preparation of a laminated, thermally cross-linked sponge consisting of a mixture of collagen and a mucopolysaccharide (GAG) is described by Boyce (U.S. Pat. No. 5,273,900). A mixed collagen and chondroitin-6-sulfate solution was deep frozen and lyophilized. It then was cross-linked at 105° C. A mixed collagen and mucopolysaccharide solution, additionally containing 3% dimethyl sulfoxide (DMSO), was sprayed onto a flat Mylar surface, frozen and the cross-linked sponge then placed onto the frozen solution.

Yoshizato (U.S. Pat. No. 5,350,583, U.S. Pat. No. 5,263,983) discloses coating denatured atelocollagen sponges, with or without a supporting layer, with a silicone permeation controlling layer.

Rosenthal (U.S. Pat. No. 5,565,210) describes composites comprising a collagen sponge construct having embedded therein oriented substructures of solid collagen fibers, films or flakes. The substructures are oriented so as to provide a scaffold for directional cellular migration into the implant. The composites are formed by immersing the substructures in an aqueous collagen suspension and then freeze-drying the suspension to form the porous collagen sponge matrix.

In Japanese Publication No. 02-071749 (JP 2071749A, application no. JP 88222538), inventor Koide Mikio, published Mar. 12, 1990, a porous collagen layer on top of a porous collagen/denatured collagen substrate is described. Both layers are porous to allow the transmission of nutrients and fluids from a wound surface to the top of the dressing.

Eisenberg, in U.S. Pat. No. 6,039,760, U.S. Pat. No. 5,282,859, and RE 35,399, discloses a process for preparing a collagen sponge that has been cross-linked by thermal dehydration. The sponge is laminated on one surface with a thin layer of high purity, preferably pepsin treated, non-porous collagen. The sponge and the layer are then dried to complete the lamination of the collagen. The sponge is then inverted and inoculated with fibroblast cells and allowed to culture. The sponge is inverted once again and keratinocytes are inoculated on the non-porous layer and allowed to culture.

SUMMARY OF THE INVENTION

The present invention relates to a collagen construct having a structure suitable for use as a biologically active skin wound dressing or a skin equivalent, for example, and the process for preparing said construct. Prior to actual use as a biologically active wound dressing or skin equivalent, the construct is inoculated with appropriate cell types in and/or on the surface thereof that produce growth factors and other bioactive substances. Such biologically active products can be used in many different applications that require the regeneration of dermal tissues. They have been used in the repair of injured skin and difficult-to-heal wounds, such as burn wounds. venous stasis ulcers or diabetic ulcers. The essence of the construct of the present invention is the presence of a cell-impermeable transitional collagen layer which, as will be seen later, acts as a barrier layer, between and joining two layers of collagen, one of which is a porous sponge layer and the other a thin surface forming the outer boundary of the transitional layer. Most preferably, the cell-impermeable transitional layer has deposited thereon a very thin layer of acid-soluble collagen which acts as a cell attachment layer. Thus, the construct in its basic form, is a bilayered device which in its most preferred form carries a thin layer as a site for cell attachment. The process of the present invention is a cost effective, efficient process amenable to large-scale manufacture of the skin substitute.

The term "bilayered" as used herein is intended to mean a construct comprising the collagen porous sponge attached to a cell-impermeable transitional or barrier collagen layer having a boundary surface. The boundary surface is the outer surface of the transitional layer opposite to the interface between the sponge and the transition layer. The bilayered construct may or may not have a cell attachment layer on the boundary layer.

The term "non-porous" as used herein is intended to mean that the object so referred to is impermeable to the migration of human cells therethrough.

Referring to the construct of this patent, the terms "permeable" and "impermeable" as applied to the sponge and its transition layer, refer to materials which have pores large enough to be ingrown by cells (permeable) and, respectively, pores, if any, which are small enough so that cells can not migrate through them (impermeable).

The term "sponge" is intended to mean a structure having spaces therein capable of permitting the migration and growth of human fibroblasts therein.

To manufacture large numbers of such devices economically, the present invention permits the use of a larger sponge than is normally used in the art, i.e., about one by two feet, which can be divided into smaller pieces of skin equivalent after the cell culturing process is completed.

The product of the present invention is a lyophilized construct comprising a collagen sponge, preferably bovine collagen, and a cell-impermeable layer having a boundary surface with the boundary surface being separated from the sponge section by the transitional layer which is produced when the sponge is placed on a collagen dispersion cast on a flat plate and dried. Most preferably, the boundary surface has deposited thereon a thin cell attachment layer. The thin cell attachment layer is comprised of acid-soluble collagen and acts to provide a keratinocyte-hospitable "third" layer of the construct. A commercially available, sterile bovine collagen (VITROGEN™) suitable for the third layer is available from Cohesion, Inc. of Calif. The bilayered construct is preferably DHT cross-linked after formation. If the sponge layer portion has been previously cross-linked, the transitional and the thin acid soluble collagen cell attachment layer may be subsequently cross-linked using other means such as ultraviolet radiation. The finished bilayered sponge (with or without the cell attachment layer) is packaged and preferably radiation sterilized. Appropriate cells such as human keratinocytes can then be cultured on the cell attachment layer and human fibroblasts cultured in the sponge matrix as described herein.

The present invention thus involves new bilayered collagen constructs and new processes therefore wherein the surface of a preformed sponge is partially "melted" or compacted into a collagen dispersion, under controlled conditions, to yield a construct in which the sponge becomes fused to and intermingled with a cell-impermeable transition layer of desired or controlled depth connected to the sponge, the transition layer terminating in a boundary surface which may or may not be, but most preferably is, further enhanced with a cell attachment layer deposited thereon.

The reason that a cell attachment layer is sometimes used, is that the boundary surface of the transitional layer may not be suitable for some purposes involving keratinocyte cell attachment. In fact, in the present invention, it is most preferred that a separate cell attachment layer comprising a very thin coating of keratinocyte-compatible, enzymatically solubilized acid-soluble collagen such as VITROGEN™ be present on the boundary surface of the transitional layer and stabilized by drying and/or by cross-linking, thus providing a "third" layer. Large amounts of expensive VITROGEN™, otherwise needed to form a cell-impermeable barrier, are avoided by virtue of the present invention which provides a cell-impermeable transition layer that may or may not (depending upon the cell type) require thin acid soluble collagen layer, thus effecting substantial cost savings.

The new process is simpler than the art process and does not require complex, labor intensive and time consuming processing under aseptic conditions preventing economical production of large amounts of bilayer sponge. The new process avoids problems such as gel invagination into the porous sponge and incomplete barrier formation that may occur using the art-known processes.

DETAILED DESCRIPTION OF THE INVENTION

Figure 1:
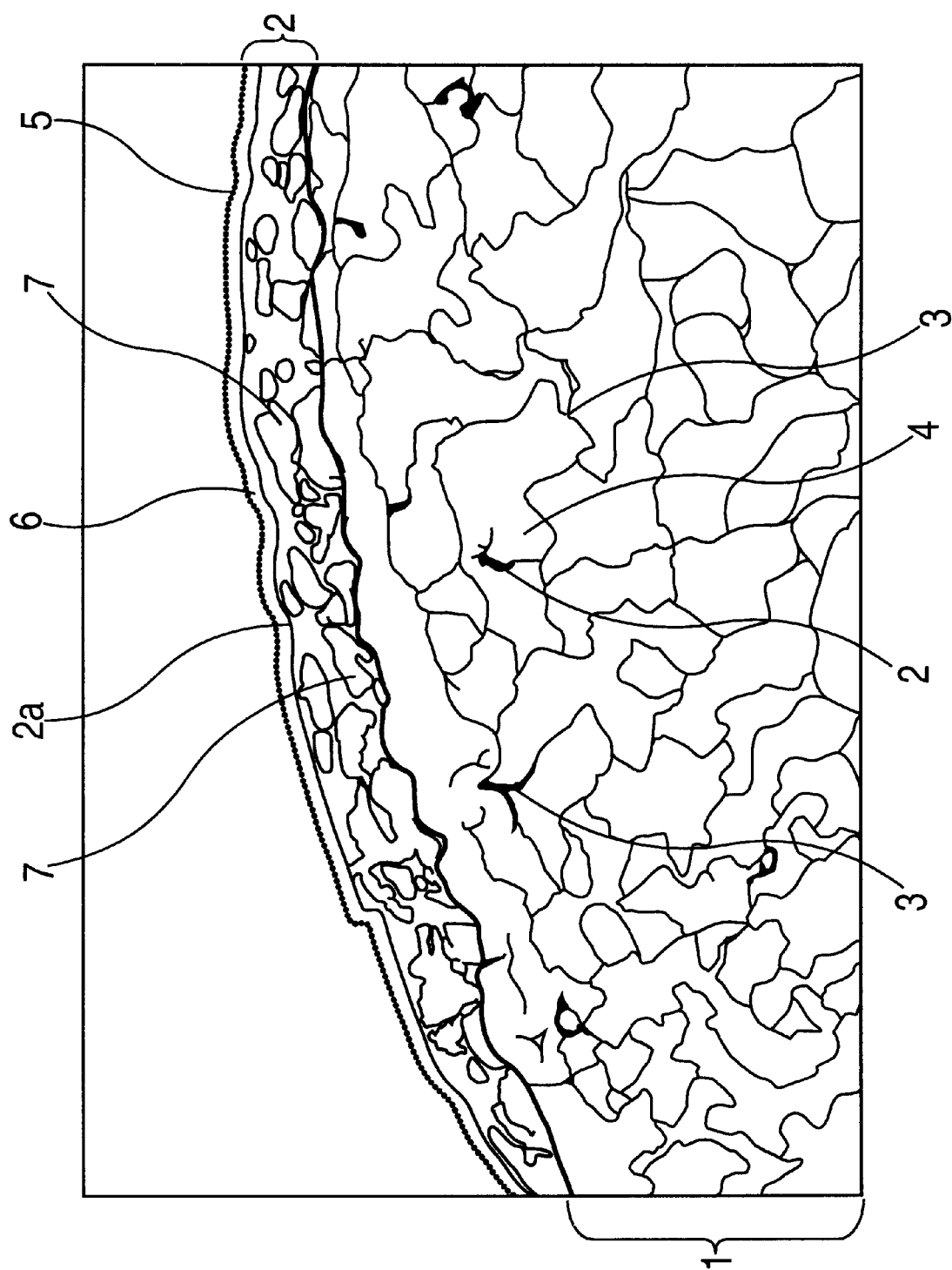
FIGS. 1 and 2 are histological cross-sections of a bilayered construct of the invention that contains a cell-impermeable transition layer and sponge. This construct was prepared by coating a dry, uncross-linked collagen sponge with a relatively thick layer of an aqueous, insoluble collagen dispersion (~25 micron wet thickness) in the manner described hereinafter.

The construct of this invention comprises a porous collagen sponge attached to a cell-hospitable collagen surface by means of an intermediate cell-impermeable transitional layer. The presence of this transitional layer is a feature which distinguishes the construct of the present invention from those of the prior art. Applicants are unaware of any bilayered collagen structure which contains such a transitional layer. The transition layer is cell-impermeable or non-porous and is the portion of the construct that merges or conjoins the cell-permeable sponge layer with the cell-hospitable surface layer. The transition layer terminates in a boundary layer or surface.

The cell-hospitable surface is ordinarily the cell attachment surface to which keratinocytes will ultimately attach and is an important component of the construct. A most preferred embodiment of the invention provides on the transitional layer, a third layer to which the cells may anchor upon which the cells may differentiate. This "third" keratinocyte attachment layer may be comprised of various materials, e.g., extracellular matrix molecules, such as laminin and various forms of collagen. Most preferably, acid soluble, bovine corium from which the telopeptide ends have been removed (atelocollagen) and commercially available as VITROGEN™, is used as the third or cell attachment layer. It has been found that atelocollagen promotes the attachment of keratinocytes to a greater extent than does Type I, II, or III insoluble collagen.

Atelocollagen is, however, considerably more expensive than Type I, II, or III insoluble collagen. For that reason, it may be desirable to form the cell-impermeable transitional barrier layer of a mixture of Type I, II, and III insoluble collagen instead of creating a relatively thick layer of atelocollagen on top of the outer surface of the collagen sponge. Thus, acid-soluble collagen may be deposited on the impermeable boundary surface of the transition layer by spraying a dilute solution (e.g. 0.01% to 0.05%) containing the acid-soluble collagen onto the surface of the transition layer or by adding it to the insoluble collagen transition layer coating dispersion, before lamination, onto the sponge and allowing a portion of the soluble collagen to partition to the surface of the transition layer during the drying process. In any case, suitable thicknesses of this third layer are within the discretion of the user, but it is preferred mostly because of cost and size consideration, to stay below about 5 microns. Larger thicknesses may be employed, if desired.

Controlling the processing variables of the bilayered construct preparation also controls the morphology and thickness of the transition layer. The thickness and pore morphology of the transition layer can be varied by employing: 1) either a non-cross-linked or a cross-linked collagen sponge, 2) varying the thickness of the insoluble collagen dispersion that is coated onto the sponge substrate, and 3) varying the concentration of collagen in the coating dispersion. A convenient range of laminating dispersion thickness has been found to be preferably between about 10 to about 30 microns wet thickness using a 1% insoluble collagen dispersion. Increasing or decreasing the concentration of collagen in the laminating dispersion will shift the range of transitional layer thickness.

Cultures of keratinocytes using constructs before and after the application of the acid soluble collagen cell attachment layer, show that attachment and differentiation of these cells is significantly increased when the acid-soluble layer is used.

The ultimate use for this construct is as a biologically active wound dressing or a skin equivalent or substitute. As such it is desirable to inoculate the sponge layer with suitable dermal cells and growth promoters and to inoculate the surface of the cell attachment layer with keratinocytes or other appropriate cells. Thus, prior to use, the construct is inoculated with appropriate cells and growth promoters within the porous sponge layer and with epidermal cells (keratinocytes) on the exterior of the boundary layer or the cell attachment layer. After culturing the inoculated construct, the finished biologically active construct is ready to be used or cryogenically stored for use as appropriate.

Since the porous sponge contacts the wound bed, it should be non-immunogenic and possess certain other physical properties. It is, for instance, desirable to form the porous sponge from a material which initially wets and adheres to the wound bed. This avoids pockets that may later become sites of bacterial growth. Close contact of the sponge with the wound surface confers a certain amount of stability to the biologically active wound dressing, thus preventing the movement of the graft relative to the wound surface. Close contact with the wound can be achieved by using materials that possess the property known as "drape". The porous. non-immunogenic, sponge layer should be insoluble in the presence of body fluids, but be slowly degradable in the presence of body enzymes. The sponge should have interconnected pores large enough for cell infiltration throughout the sponge.

Collagen is a major protein constituent of connective tissue in vertebrates. Typical commercial animal sources include the bovine Achilles tendon, calfskin and the bones of cattle. The collagen used in the preparation of the porous sponge may be Type I, Type II or Type III collagen. Bovine Type I collagen is preferred for the preparation of the porous sponges of this invention.

Because open wounds tend to lose moisture very rapidly, a biologically active skin equivalent or wound dressing must be able to retard that loss. In effect, the biologically active wound dressing ideally should match the moisture transmission rate for normal skin. Should the normal transmission rate be greatly exceeded, the host tissue in the neighborhood of the graft and the graft itself will become dehydrated. If the moisture transmission rate is much lower than normal, edema may result.

Since a porous sponge has a high moisture transmission rate, a moisture transmission barrier needs to be attached on one side of the sponge. This barrier membrane should possess a moisture transmission rate that can be controlled to be close to that of normal skin. It should be intimately attached to the porous sponge and not separate over time in a moist wound. Furthermore it's physical properties should be such that the whole construct is compliant with the wound and is easily "draped". It goes without saying that the moisture transmission barrier must be non-immunogenic. The transition layer with its outer boundary surface layer serves this purpose and acts as a barrier layer.

As is the case with the first sponge layer, collagen is also a suitable material for the impermeable transition layer. The collagen used for preparing the impermeable layer and the transition region may be of Type I, Type II or Type III insoluble collagen or other collagenous materials such as atelocollagen or mixtures of any of these.

The transition layer is created during the process of bonding the collagen from a suspension or dispersion to the collagen sponge. The transition layer comprises material from both the sponge and the dispersion. This produces a construct that has the transition layer interlocked with the porous sponge. The advantage of this interlocked structure is that the transition layer is firmly attached to the sponge and will not separate from the sponge during the subsequent cell inoculation and culturing steps or during use. This preferred structure of the transition layer is achieved by placing a porous sponge, which preferably has not yet been cross-linked, onto an aqueous suspension of the appropriate collagen and letting the sponge and suspension dry. During this process the sponge imbibes the suspension and, in doing so partially collapses or "melts" owing at least in part to the non-crosslinked nature of the sponge. This process should be carefully controlled so as not to create too thick or too thin an impermeable layer. The former would reduce the depth of the porous sponge to an undesirable degree, while the latter would endanger the properties of the transition layer needed for a desirable moisture transmission rate. This moisture transmission rate allows transport of nutrients and byproducts such as cytokines and growth factors between the cell permeable sponge and the surface of the cell-impermeable layer. In extreme cases of a transition layer that is too thin, it may actually contain pores large enough to allow cell migration. For the constructs of the invention, thicknesses of sponges are suitably in the range of about 1 to 3 mm while thicknesses of the dry transition layer suitably range from about 10–30 microns.

To produce the transitional layer, the collagen suspension, which will ultimately form the layer, is poured onto a flat, horizontal release substrate. The suspension is then cast into a wet film of a desired thickness with the aid of a blade type applicator. The porous sponge is then carefully placed on top of the suspension. The thickness of the suspension under the substrate, the temperature at which the operation is carried out, the collagen concentration of the suspension and the degree of cross-linking of the sponge, all control the degree to which a sponge is allowed to imbibe the collagen suspension. The sponge and the formative transition layers are dried and then may be placed in an oven to cross-link all the layers. Alternatively the transition layer, before or after drying, may be sprayed with a mist of acid soluble atelocollagen to form the "third" cell attachment layer typically of between about 1 and 5 microns and the construct then subjected to standard cross-linking by heating.

The flat substrate onto which the collagen suspension is cast is preferably made of a uniform material such as polyethelene terephthalate glycol (PETG), which will cleanly release the barrier layer and sponge after the drying step has been completed. The nature of the material from which the substrate is constructed should allow the collagen solution to wet the substrate smoothly and be released cleanly of the transition film without disrupting the structure.

When the substrate is flat and smooth, the surface of the transition layer is smooth and shiny. Other textures of the substrate can be used for the transition layer to mirror roughness, grooves, or other designs.

Cross-linking of the construct can be achieved by chemical means, exposure to UV radiation, or other suitable means. In the process of this invention, however, dehydrothermal (DHT) cross-linking is preferred when the sponge has not been previously cross-linked. To achieve dehydrothermal cross-linking, the moisture level of the construct is reduced to a very low level by subjecting the construct to elevated temperatures and high vacuum. This process eliminates the need for introducing potentially toxic chemical cross-linking agents, which may, after completion of the reaction, have to be removed.

The cross-linking step serves as a mechanism to "lock in" the structure of the matrix. This prevents shrinkage of the pores and the collapse of the sponge, which could occur with an un-cross-linked construct upon tissue culture, storage or use. The effect of the cross-linking step on the transitional layer is to strengthen the bond between the sponge and the transition layer and to prevent future dimensional changes in these layers.

The construct is then sterilized and inoculated with suitable cell types and, optionally, a cocktail of cytokines, growth factors and extracellular construct substances.

An advantage of this construct is that it is easy to produce in large quantities and can be used in processes for the production of the cell containing biologically active wound dressings and other therapeutic devices such as blood vessels.

In general, the processes of the prior art tend not to promote the formation of an intermediate transitional region. As noted above, the transitional layer of the construct of the invention requires a partial collapse of the sponge surface and a blending thereof into the applied layer. The direct application of the sponge onto the wet collagen layer with subsequent drying and crosslinking avoids intermediate steps which are costly and labor intensive.

Another advantage of the construct of this invention is that it can be in the form of large sheets with a transitional layer of controlled thickness as opposed to that obtained by dropping or applying solutions onto a sponge surface. After incubation of a large sheet of construct with appropriate cells, the large sheet can be cut into the desired sizes and shapes and the individual pieces used or cryogenically stored.

DETAILED DESCRIPTION OF THE DRAWINGS

FIG. 1 is a cross-section, at a 4X magnification, of a bilayered construct of the invention wherein the sponge used was not cross-linked prior to application of the cell-impermeable transition layer. The porous sponge (1) occupies the major part of the structure. A second layer, i.e. a cell-impermeable transition layer (2) is attached to the sponge and intermeshes therewith. The physical structure of the sponge consists of thin walls (3) and large spaces (4). In the finished biologically active skin substitute or equivalent, these spaces may be filled with cells such as dermal cells as well as growth factors and other products of cell metabolism. On the boundary surface (2a) of the cell-impermeable transition layer (2), is a cell attachment layer (6) coated with keratinocytes (5) seen as a layer of dark dots on top of the cell attachment layer (6). Layer (6) is not visible at this magnification on the boundary surface (2a) of the cell-impermeable transition layer (2).

The physical structure of the transition layer shows a dense, compact structure containing fewer and more compact open spaces (7) than those (4) of the sponge. The gradient of gradually decreasing numbers of spaces (7) as one proceeds from the intermeshing interface with the sponge through the transitional layer (2) is apparent. At the interface, the line is somewhat diffuse and contains open spaces more similar in quantity to that existing in the sponge reflecting the "collapse" or "melting" of the sponge surface into the lamination layer during preparation. As one traverses the transition layer, the open spaces become fewer in number until they are no longer present at the top continuous boundary surface (2a) of the transition layer (2).

Figure 2:
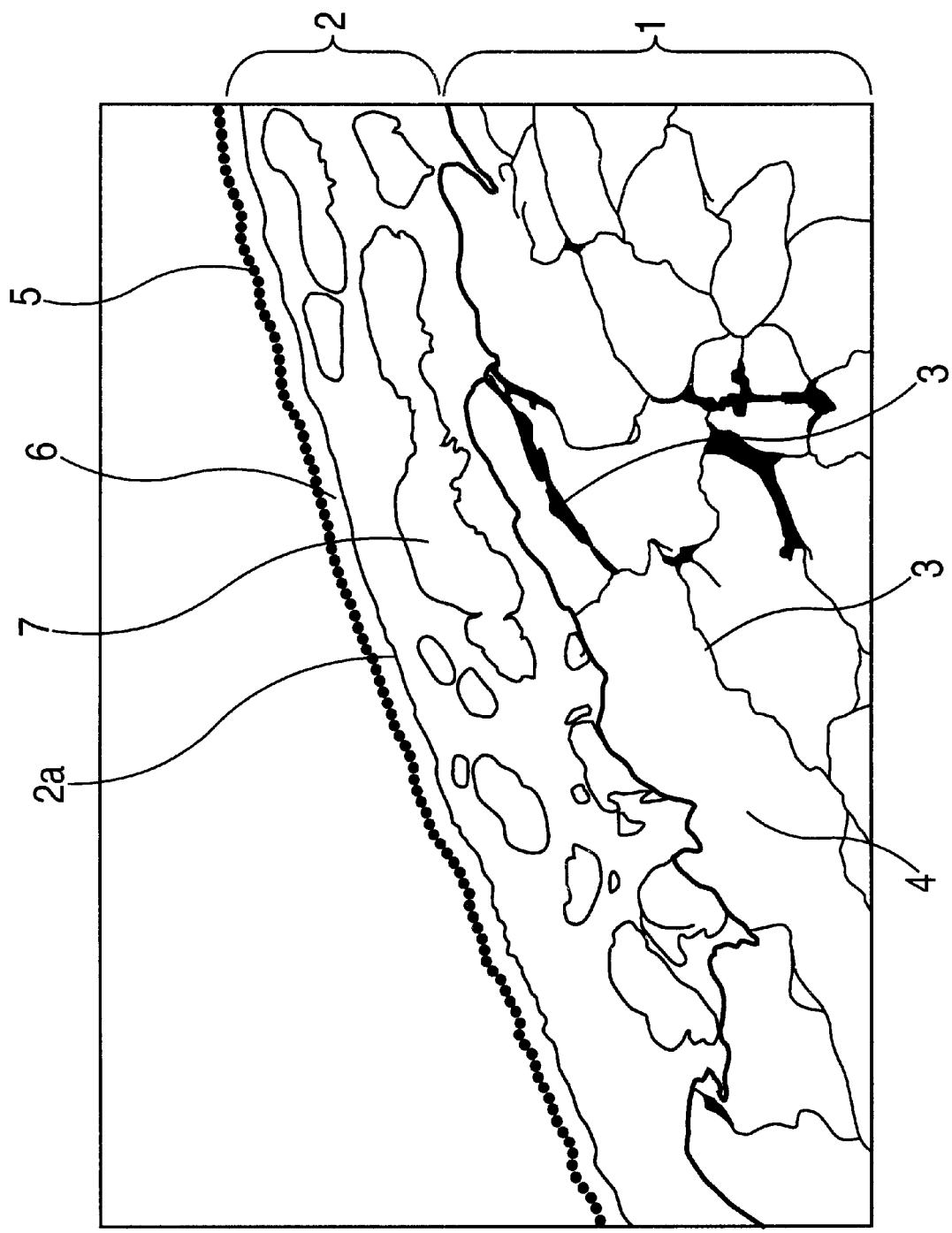

FIG. 2 is a 10X magnified cross-section of a sponge of this invention showing the transition layer (2) in more detail. The delicate walls (3) and large spaces (7) are apparent in the sponge layer. The transitional layer (2) with its boundary surface (2a) is between the porous sponge (1) and the cell attachment layer (6). This transitional layer (2) is anchored to the porous sponge layer (1) and consists of an intermingling of the source materials used for the porous sponge and the impermeable transitional layer. Keratinocytes (5) can be seen covering the cell attachment third layer (6).

Figure 3:
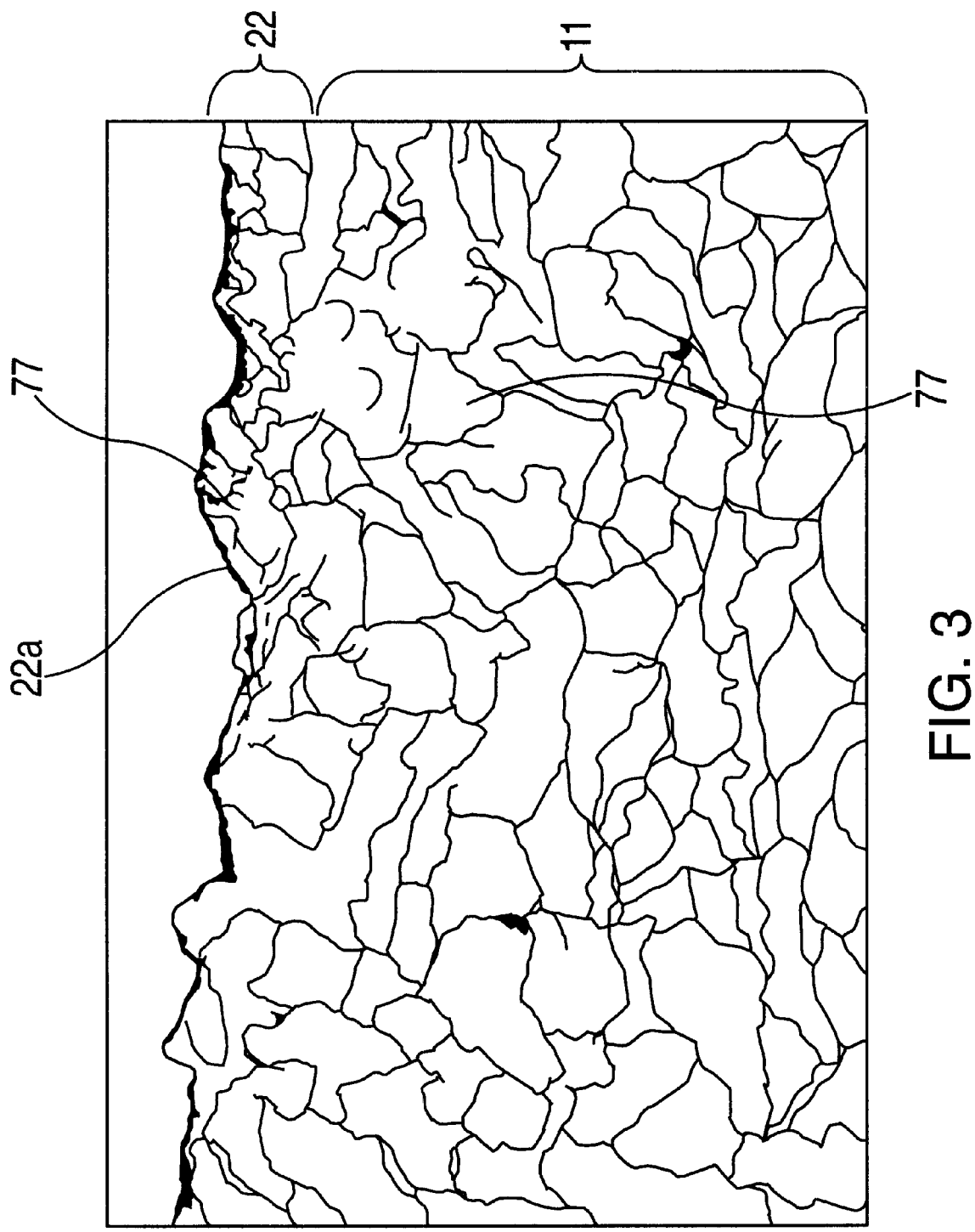
FIG. 3 depicts a construct in which the transition layer is relatively thin and only slightly porous but still cell-impermeable. This construct was prepared by applying a DHT cross-linked collagen sponge to a relatively thin layer of aqueous, insoluble collagen dispersion (~15 microns wet thickness).

FIG. 3 is a histological cross section of a bilayered construct of the invention wherein the sponge was cross-linked by DHT prior to application to the aqueous collagen dispersion which would ultimately form the transition layer (22) terminating in a boundary surface or cell attachment surface (22a). The cell-impermeable transition layer (22) is distinguishable from the cell-permeable or sponge layer (11) and shows an undulating region of which the top boundary surface (22a) is a part constituting the transition layer (22) wherein the open spaces (77) are more compact than in cell-permeable layer (11). Relative to FIG. 1, the cell-impermeable transition layer is thinner which is generally the result of using a previously DHT cross-linked sponge reflecting the property of the latter to produce reduced compaction of the cell-permeable sponge layer (11) when pressed into the aqueous laminate suspension.

Deposited on surface (22a) is a cell attachment layer which is very thin and not visible at the magnification of FIG. 3. The acid soluble collagen comprising that third layer as an enhanced cell attachment layer is deposited as a fine mist of about a 0.03% solution on surface (22a). There results an extremely thin third layer in low microns range.

The process of the present invention is illustrated as follows:

An aqueous lamination suspension of collagen powder consisting of a mix of Type I and III insoluble bovine collagen having a solids content range of 0.75–1.5% is prepared at a pH of about 3.0, preferably ±0.2, in a bowl chopper under high vacuum, mixed at high speed of 2,000–3,000 rpm, preferably 2,400 rpm until blended (30 seconds to 1 minute). If the lamination suspension is to contain the optional attachment layer such as is provided by the acid soluble atelocollagen (VITROGEN™), it is then mixed in at the desired ratio, range 4:1 collagen suspension:VITROGEN™ to 12:1 collagen suspension:VITROGEN™. When the laminating suspension is to be used with a sponge that has been crosslinked before the lamination process, the higher end of the solids content range is preferred.

Casting of the lamination suspension procedure applies to both straight collagen lamination as well as the collagen/VITROGEN™ mix lamination. The laminating suspension is placed onto a clean PETG horizontal sheet (substrate may be any material that allows for an easy release of the dried collagen material).

A blade applicator, such as a Gardco Blade Applicator, is set with the blade to the desired gap height (range about 10–30 microns) on the substrate slightly in front of the dispensed laminating suspension. The applicator is drawn horizontally to create a thin wet film of the laminating suspension. The collagen sponge is then placed on top of the thin wet film. When using a pre-DHT sponge, care should be taken since the sponge is fragile and may collapse if too much force is applied. When using a post-DHT sponge, firm pressure may be applied to the top of sponge to ensure good contact between the laminating suspension and the sponge. The sponge/film complex may be dried in a convection oven at 35° C. for several hours.

If the laminating suspension does not contain VITROGEN™ and an enhancement layer is desired, a fine mist of VITROGEN™ may be sprayed onto the laminate surface.

Cross-linking of laminate:

If a pre-DHT sponge has been laminated, then the whole construct must be cross-linked. DHT, UV or other cross-linking methods may be used as is known in the art.

If post-DHT sponge has been laminated, the laminate may be cross-linked by DHT, UV, or other methods with UV being preferred.

UV crosslinking: Exposure of the laminate surface of sponge to UV light (254 nm) for 1–12 hours produces suitable results.

DHT cross-linking of laminate: DHT at 110° C. for 6–24 hours.

EXAMPLES

The following examples show various ways in which the product of this invention can be made.

Example 1

The following steps describe the process for preparing a collagen sponge construct of this invention consisting of a porous collagen sponge and a cell-hospitable attachment surface layer with a transitional layer between the sponge and the cell-hospitable layer.

A collagen sponge suspension of Type I collagen or a mixture of Type I, II, and III insoluble collagen at 0.75–1.5% preferably above 1% solids is prepared by mixing in a bowl chopper under vacuum. Once mixed, 35–40 g of suspension is poured into a 3" by 3" sponge mold. The mold is then rapidly cooled to about −45° C. and lyophilized for 24 hours under vacuum. The sponge is then removed from the mold.

To form the transitional layer, a 1% collagen suspension is prepared from collagen powder according to the sponge suspension processing conditions described above. The suspension is poured onto a sheet made from PETG (polyethylene terephthalate glycol). A blade applicator set with a gap height preferably between 10 to 30 microns is used to spread a thin wet film. The collagen sponge, prepared above, is carefully placed onto the wet film of the collagen suspension. Applying light pressure to the sponge will ensure good contact between the sponge and the wet film.

The sponge/barrier layer complex is placed into a convection oven at a temperature of about 35° C. until the sponge/barrier layer complex is completely dry. This non-cross-linked construct is then DHT treated at a temperature of 110° C. for 168 hrs. The DHT treatment serves as a mechanism to "lock-in" the structure of the construct by means of cross-linking. The construct can then be γ-sterilized for use in tissue culture.

Example 2

This example shows the preparation of another construct of this invention. This construct consists of a porous collagen sponge layer, a transitional layer between the sponge and a thin layer of atelocollagen at least partially covering the outer surface of the transitional barrier layer.

A porous sponge is prepared in accordance with the directions given in Example 1. The cell-impermeable layer is applied as before and the dry cell-impermeable layer side of the non-cross-linked construct is sprayed with a 0.3% atelocollagen solution in aqueous medium. It is desirable to create as thin a layer of atelocollagen as possible, preferably less than 5 microns. The construct, which now contains a cell-hospitable layer, is DHT treated as in Example 1.

What is claimed is:

1. A process for preparing a collagen construct comprising a porous, cell-permeable collagen layer, a cell-impermeable transitional collagen layer, and a cell-hospitable attachment layer comprising a collagen material which is different from the collagen material of the cell-impermeable transitional layer which comprises
    a) providing a collagen suspension on a surface and placing a porous; cell-permeable collagen sponge thereon, whereby the porous, cell-permeable sponge imbibes the suspension to a desired depth into the sponge,
    b) drying the collagen suspension on the porous, cell-permeable sponge thereby creating on the cell-permeable collagen sponge a cell-impermeable collagen layer connected to said collagen sponge via a transition layer having an external surface, and
    c) applying to the external surface of the cell-impermeable layer a solution of a collagen material which is different from the collagen material of the cell-impermeable transitional layer and drying the resulting construct.

2. The process according to claim 1 wherein the cell-hospitable cell-attachment layer is atelocollagen.

3. The process of claim 1 wherein the collagen sponge is uncross-linked prior to step (a) and the process includes the additional step (step d) of cross-linking the construct any time after step (a).

4. The process of claim 3 wherein step (d) is performed after step (c).

5. The process of claim 2 wherein the cell-permeable collagen layer is cross-linked before step (a) and the cell-impermeable transitional layer is cross-linked any time after step (a) and the cell attachment layer is cross-linked any time after step (c).

6. The process of claim 5 wherein the transitional layer and the cell attachment layer are cross-linked together after step (c).

7. The process of claim 3 wherein the cross-linking is achieved by dehydrothermal cross-linking.

8. The process of claim 1 wherein the collagen suspension of step (a) includes atelocollagen and the process includes the further step of allowing the atelocollagen to partition from the collagen suspension before or after the collagen sponge is placed on said collagen suspension.

9. The process according to claim 1 wherein each of the porous, cell-permeable layer and the cell-impermeable transitional layer is the same or different material selected from the group consisting of type I collagen, type II collagen, type III collagen, atelocollagen, and mixtures thereof, and the cell-attachment layer material is different from the cell-impermeable layer material.

10. A construct comprising a porous, cell-permeable sponge layer attached to a transitional layer comprising a cell-impermeable collagen layer, said impermeable layer terminating in an external boundary surface and a cell-attachment layer comprising on said external boundary surface as a third layer of said construct, a collagen material which is different from the collagen material of the cell-impermeable transitional layer.

11. The construct of claim 10 wherein the cell attachment layer is atelocollagen.

12. A collagen construct in accordance with claim 11 wherein the collagen of the porous, cell permeable layer, the transitional layer, and the cell attachment layer are cross-linked.

13. A collagen construct in accordance with claim 12 wherein each of the porous, cell-permeable layer and the cell-impermeable transitional layer is the same or different material selected from the group consisting of type I collagen, type II collagen, type III collagen, atelocollagen, and mixtures thereof and the cell-attachment layer is different from the cell-impermeable transitional layer.

14. The collagen construct of claim 13 which further comprises living cells within the porous sponge and different living cells on the cell attachment layer.

15. The collagen construct of claim 14 wherein cells in the porous sponge are dermal cells and the cells on the cell attachment layer are epidermal cells.

16. The process of claim 12 wherein the cross-linking is achieved by dehydrothermal treatment (DHT) or UV radiation.

17. The construct of claim 13 wherein the cell-attachment layer is atelocollagen.

18. The construct of claim 15 wherein the collagen of the porous, cell-permeable layer, the transitional layer, and the cell-attachment layer are each cross-linked.

19. The construct of claim 16 wherein the cell-attachment layer is about 5 microns or less in thickness.

20. The process of claim 2 wherein the solution of atelocollagen is applied in step c) as a solution of from 0.01% to 0.05% of collagen.

* * * * *

UNITED STATES PATENT AND TRADEMARK OFFICE
CERTIFICATE OF CORRECTION

PATENT NO.     : 6,500,464 B2
DATED          : December 31, 2002
INVENTOR(S)    : Ralph A. Ceres, David J. Brown and Daniel C. Lesnoy It is certified that error appears in the above-identified patent and that said Letters Patent is hereby corrected as shown below:

<u>Title page, Item [54] and Column 1, line 1,</u>
The title "BILAYERED COLLAGEN CONSTRUCT" should read
-- ...TRILAYERED COLLAGEN CONSTRUCT... --

<u>Column 12,</u>
Line 9, the word "porous;" should read -- ...porous,... --

Signed and Sealed this

Twenty-fifth Day of March, 2003

JAMES E. ROGAN
*Director of the United States Patent and Trademark Office*